(12) United States Patent
Damon et al.

(10) Patent No.: US 6,689,897 B2
(45) Date of Patent: Feb. 10, 2004

(54) INTERMEDIATES OF CETP INHIBITORS

(75) Inventors: David B. Damon, Mystic, CT (US); Robert W. Dugger, Stonington, CT (US); Robert W. Scott, San Diego, CA (US)

(73) Assignee: Pfizer Inc., New York, NY (US)

( * ) Notice: Subject to any disclaimer, the term of this patent is extended or adjusted under 35 U.S.C. 154(b) by 70 days.

(21) Appl. No.: 10/137,314

(22) Filed: Apr. 30, 2002

(65) Prior Publication Data

US 2002/0177716 A1 Nov. 28, 2002

Related U.S. Application Data

(60) Provisional application No. 60/287,522, filed on Apr. 30, 2001.

(51) Int. Cl.$^7$ .................... C07C 229/00; C07C 255/00; C07D 215/16
(52) U.S. Cl. .................. 560/43; 558/389; 564/163; 546/159
(58) Field of Search .................. 558/389; 564/163; 560/43; 546/159

(56) References Cited

U.S. PATENT DOCUMENTS

| | | | |
|---|---|---|---|
| 6,140,343 A | 10/2000 | DeNinno et al. | ........... 514/313 |
| 6,197,786 B1 | 3/2001 | DeNinno et al. | ........... 514/313 |

FOREIGN PATENT DOCUMENTS

| | | | | |
|---|---|---|---|---|
| WO | WO 0002887 | 1/2000 | ............. | C07F/9/02 |
| WO | 0017164 | * 3/2000 | | |
| WO | 0017165 | * 3/2000 | | |

OTHER PUBLICATIONS

Gordon, D. J., et al, Circulation, vol. 6, pp. 8–15 (1989), "High–density Lipoprotein Cholesterol and Cardiovascular Disease."

* cited by examiner

*Primary Examiner*—Paul J. Killos
(74) *Attorney, Agent, or Firm*—Peter C. Richardson; Gregg C. Benson; Lisa A. Samuels

(57) ABSTRACT

This invention relates to intermediates useful in the preparation of CETP inhibitors and methods of preparation thereof.

21 Claims, No Drawings

INTERMEDIATES OF CETP INHIBITORS

CROSS REFERENCE TO RELATED APPLICATION

This application claims the benefit of U.S. Provisional Application No. 60/287,522 filed Apr. 30, 2001.

FIELD OF THE INVENTION

This invention relates to intermediates useful in the preparation of CETP inhibitors and methods of preparation thereof.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S.

Risk for development of this condition has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J., et al.: "High-density Lipoprotein Cholesterol and Cardiovascular Disease", Circulation, (1989), 79: 8–15).

High LDL-cholesterol and triglyceride levels are positively correlated, while high levels of HDL-cholesterol are negatively correlated with the risk for developing cardiovascular diseases. Thus, dyslipidernia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues resulting in reduced compliance. Fibrates and the HMG-CoA reductase inhibitors raise HDL-C only modestly. As a result, there is a significant unmet medical need for a well-tolerated agent which can significantly elevate plasma HDL levels, thereby reversing or slowing the progression of atherosclerosis.

PCT application publication number WO 00/02887 discloses the use of catalysts comprising certain novel ligands for transition metals in transition metal-catalyzed carbon-heteroatom and carbon—carbon bond formation.

Commonly assigned U.S. Pat. No. 6,140,343, the disclosure of which is incorporated herein by reference, discloses, inter alia, the CETP inhibitor, cis-4-[acetyl-(3,5-bis-trifluoromethyl-benzyl)-amino-2-ethyl-6-trifluoromethyl-3,4-dihydro-2H-quinoline-1-carboxylic acid isopropyl ester, and processes for the preparation thereof (e.g., procedure disclosed in Example 46).

Commonly assigned U.S. Pat. No. 6,197,786, the disclosure of which is incorporated herein by reference, discloses, inter alia, the CETP inhibitor, cis-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, and processes for the preparation thereof (e.g., procedure disclosed in Example 7).

SUMMARY OF THE INVENTION

One aspect of this invention is the compound of formula III,

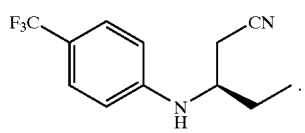

Another aspect of this invention is the compound of formula IV,

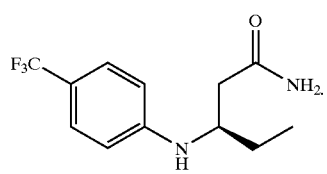

A further aspect of this invention is compounds of formula VI,

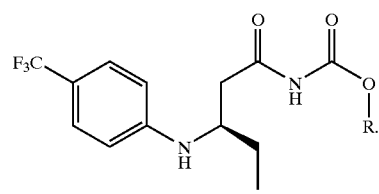

wherein R is selected from methyl, benzyl and substituted benzyl.

An additional aspect of this invention is compounds of formula VII,

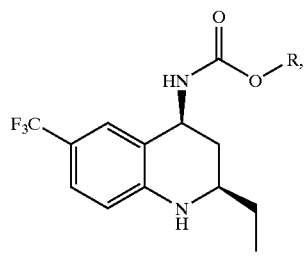

wherein R is selected from methyl, benzyl and substituted benzyl.

In a preferred embodiment of the compound aspects of this invention, R in the compounds of formula VI and the compounds of formula VII is selected from methyl, benzyl and benzyl substituted with one or more substituents each independently selected from $(C_1–C_3)$alkyl, $(C_1–C_3)$alkyloxy and a halogen.

A further aspect of this invention is methods for preparing the compound of formula 111, above, comprising coupling trifluoromethylbenzene that is para-substituted with a halogen or O-triflate with the compound of formula II,

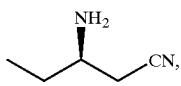

to form the compound of formula III.

In a preferred embodiment of the method aspect of this invention relating to preparing the compound of formula III said coupling of said trifluoromethylbenzene compound with said compound of formula II occurs in the presence of a transition metal, preferably palladium.

In another preferred embodiment of the method aspect of this invention relating to preparing the compound of formula III said coupling of said trifluoromethylbenzene compound with said compound of formula II occurs in the presence of a phosphine ligand, preferably a dialkylphosphinobiphenyl ligand, more preferably selected from 2-dicyclohexylphosphino-2'-(N,N-dimethylamino)biphenyl and 2-dicyclohexylphosphino-2'-methylbiphenyl.

In an additional preferred embodiment of the method aspect of this invention relating to preparing the compound of formula III said coupling of said trifluoromethylbenzene compound with said compound of formula II occurs in the presence of a base, preferably cesium carbonate.

Another aspect of this invention is methods for preparing the compound of formula IV, above, comprising hydrolyzing the above compound of formula III, with a hydrolyzing agent selected from an acid and a base, preferably an acid, more preferably sulfuric acid with water, to form the compound of formula IV.

A further aspect of this invention is methods for preparing compounds of formula VI, above, comprising combining the compound of formula IV, above, with a compound of formula V,

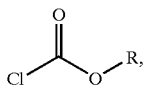

wherein R is selected from methyl, benzyl and substituted benzyl, in the presence of a base, preferably lithium t-butoxide, to form compounds of formula VI.

An additional aspect of this invention is methods for preparing compounds of formula VII, above, comprising reducing the above compounds of formula VI, wherein R is selected from methyl, benzyl and substituted benzyl, with a reducing agent, preferably sodium borohydride in the presence of a Lewis acid, preferably calcium ions or magnesium ions, to form a reduced compound and cyclizing the reduced compound under acidic conditions to form a compound of formula VII.

The term "substituted benzyl" with respect to compounds of formula V, VI and VII means benzyl that is substituted on the benzene ring with one or more substituents such that such substitution does not prevent: (a) the reaction of the applicable formula V compound with the compound of formula IV to form the applicable formula VI compounds, (b) the reduction and cyclization of the applicable formula VI to form the applicable formula VIIB compound, (c) the acetylation of the formula VIIB compound to form the formula VIIIB compound or (d) the deprotection step to remove the applicable substituted benzyloxycarbonyl group in forming the formula IB compound from the compound of formula VIIIB. Preferred substituents are ($C_1$–$C_3$)alkyl and ($C_1$–$C_3$)alkoxy and halogens.

Chemical structures herein are represented by planar chemical structure diagrams that are viewed from a perspective above the plane of the structure. A wedge line (◥) appearing in such chemical structures represents a bond that projects up from the plane of the structure.

DETAILED DESCRIPTION OF THE INVENTION

Reaction Scheme A illustrates the process for preparing the chiral isomer of formula II from (R)-2-amino-1-butanol. Scheme B illustrates the process of preparing the cholesterol ester transfer protein inhibitors of formula IA and formula IB.

SCHEME A

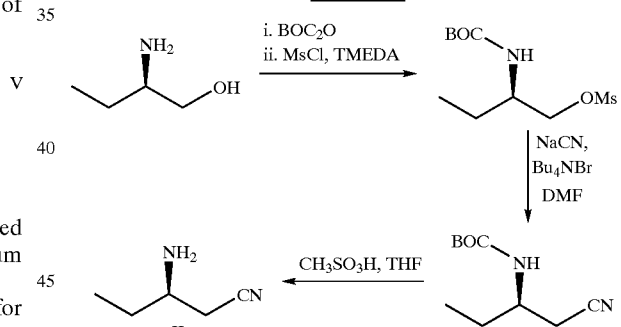

SCHEME B

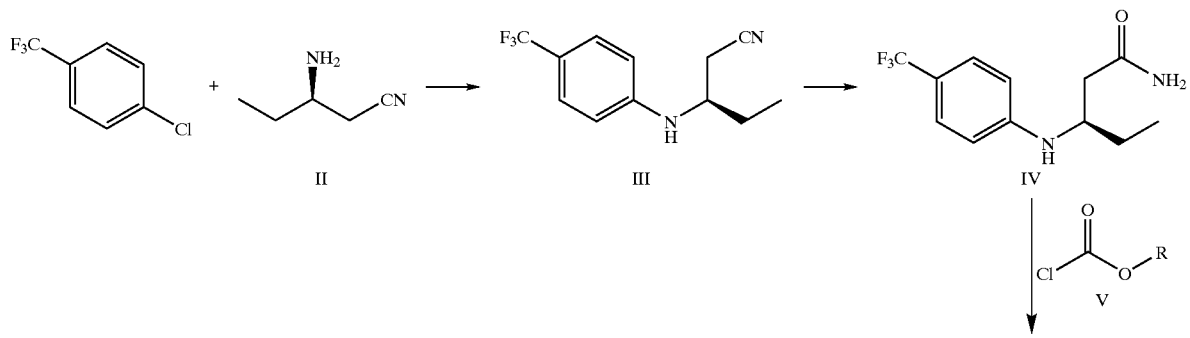

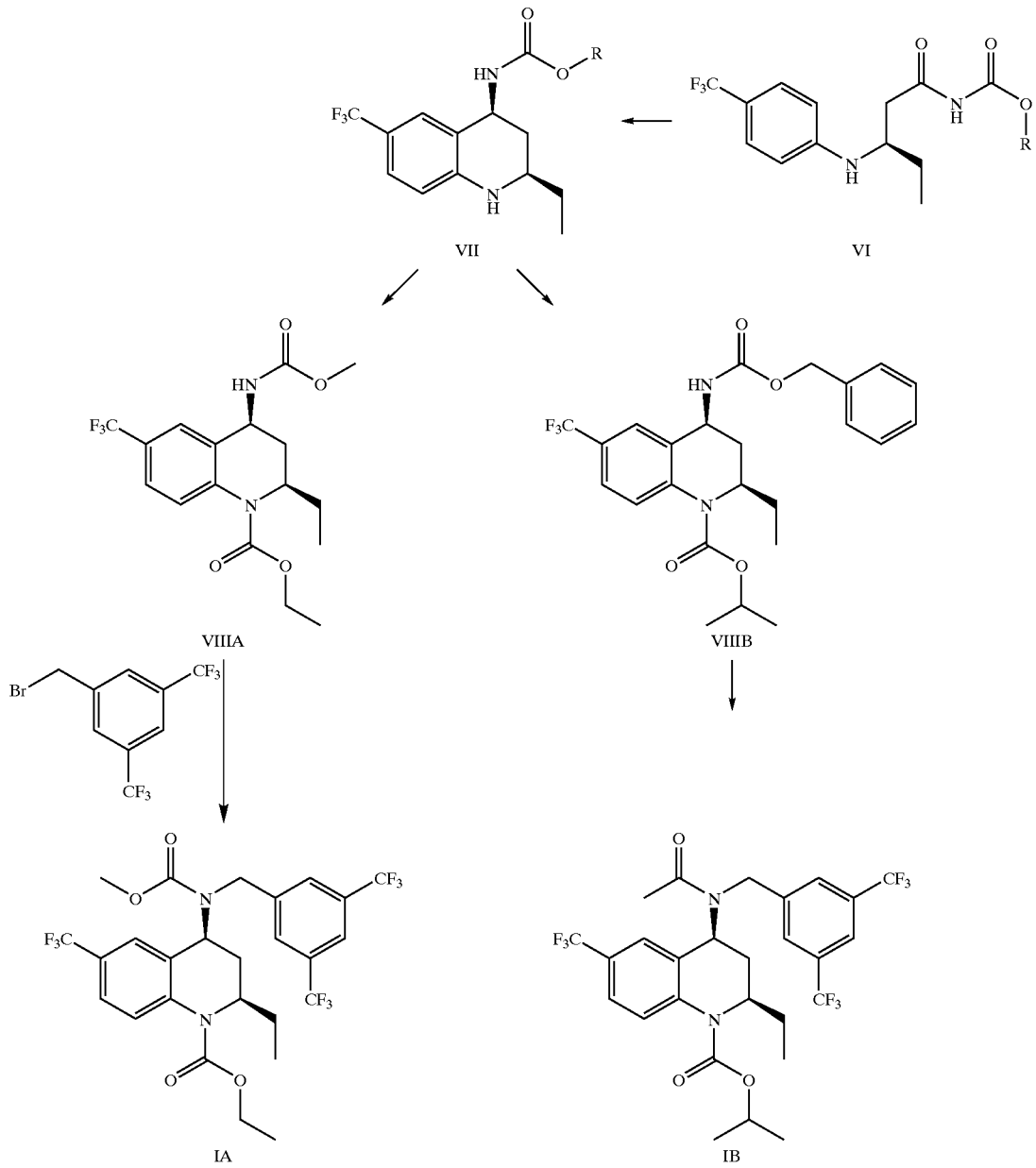

According to Scheme B, the formula III compound is prepared by combining the chiral isomer compound of formula II ((R)-3-amino-pentanenitrile) with trifluoromethylbenzene that is para-substituted with a halogen or O-triflate (—O—S(O)$_2$CF$_3$) in the presence of a metal catalyst, preferably Pd. For optimal coupling, the coupling reaction occurs in the presence of a ligand, preferably a phosphine ligand, and a base. A preferred phosphine ligand is a dialkylphosphinobiphenyl ligand, preferably selected from 2-dicyclohexylphosphino-2'-(N,N-dimethylamino) biphenyl) and 2-dicyclohexylphosphino-2'-methylbiphenyl. The reaction is preferably performed at a temperature of about 60° C. to about 110° C. The formula II chiral isomer may be prepared from (R)-2-amino-1-butanol (CAS# 005856-63-3) by methods known to those skilled in the art according to Scheme A and as described in Example 9 of the Experimental Procedures.

The formula IV compound is prepared by hydrolyzing the nitrile of the formula III compound. The hydrolysis may be performed in acidic or basic conditions. The preferred method of hydrolysis is under acidic conditions, preferably using sulfuric acid and water. For hydrolysis with base, preferred bases are hydroxy bases, preferably lithium hydroxide, sodium hydroxide and potassium hydroxide, or alkoxy bases, preferably methoxide and ethoxide. Also, for hydrolysis with base, it is preferably to use a peroxide. The hydrolysis reaction is preferably performed at a temperature of about 20° C. to about 40° C.

The formula VI compound is prepared by reacting the amide of the formula IV compound with a formula V chloroformate in the presence of a base, preferably lithium t-butoxide. The reaction is preferably performed at a temperature of about 0° C. to about 35° C. If the formula VI compound having R as methyl is desired, then methyl chloroformate is used as the formula V compound. If the formula VI compound having R as benzyl is desired, then benzyl chloroformate is used.

The formula VII compound is prepared by reacting the imide of the formula VI compound with a reducing agent, preferably sodium borohydride, in the presence of a Lewis acid activator, preferably calcium or magnesium ions to produce a reduced intermediate. The reaction to make the reduced intermediate is preferably performed at a temperature of about −20° C. to about 20° C. Under acidic conditions, the intermediate diastereoselectively cyclizes to form the tetrahydroquinoline ring of formula VII. The cyclization step is preferably performed at about 20° C. to about 50° C.

The CETP inhibitor of formula IA is prepared by acylating the compound of formula VII wherein R is methyl at the tetrahydroquinoline nitrogen with ethyl chloroformate in the presence of a base, preferably pyridine, to form the compound of formula VIIIA. The reaction is preferably performed at a temperature of about 0° C. to about 25° C.

The formula IA CETP inhibitor is prepared by alkylating the formula VIII compound, wherein R is methyl, with a 3,5-bis(trifluoromethyl)benzyl halide, preferably 3,5-bis (trifluoromethyl)benzyl bromide in the presence of a base, preferably an alkoxide or hydroxide, and more preferably potassium t-butoxide. The preferred temperature range of the reaction is about 25° C. to about 75° C.

The CETP inhibitor of formula IB is prepared by acylating compound VII wherein R is benzyl or substituted benzyl at the tetrahydroquinoline nitrogen with isopropyl chloroformate in the presence of a base, preferably pyridine, to form the compound of formula VIIIB. The preferred temperature of this reaction is about 0° C. to about 25° C.

The CETP inhibitor of formula IB may then be prepared from the formula VIIIB compound by first treating compound VIIIB with an excess of a hydrogen source (e.g., cyclohexene, hydrogen gas or ammonium formate) in the presence of a suitable catalyst in a polar solvent (e.g. ethanol) to remove the benzyloxycarbonyl group. The 3,5-bis-trifluoromethylbenzyl group of the formula IB compound may then be introduced by treating the amine and an acid, such as acetic acid, with 3,5-bis-trifluoromethyl-benzaldehyde followed by treatment with a hydride source, such as sodium triacetoxyborohydride. Then, the amino group is acetylated by methods known by those skilled in the art to form the formula IB compound. The procedure for preparing the compound of formula IB from the compound of formula VIIIB is further described in Example 46 of commonly assigned U.S. Pat. No. 6,140,343. The disclosure of U.S. Pat. No. 6,140,343 is incorporated herein by reference.

Experimental Procedures

Melting points were determined on a Buchi melting point apparatus. NMR spectra were recorded on a Varian Unity 400 (Varian Co., Palo Alto, Calif.). Chemical shifts are expressed in parts per million downfield from the solvent. The peak shapes are denoted as follows: s=singlet; d=doublet; t=triplet; q=quartet; m=multiplet; bs=broad singlet.

EXAMPLE 1

(3R)-3-(4-Trifluoromethyl-phenylamino)-pentanenitrile

A clean, dry and nitrogen gas purged 100 L glass tank was charged with (R)-3-aminopentanenitrile methanesulfonic acid salt (3000 g, 15.44 mol), sodium carbonate (2.8 kg, 26.4 mol), and methylene chloride (21 L). The heterogeneous mixture was stirred well for at least 2 hours. The mixture was filtered and the filter was rinsed with methylene chloride (3×2 L). The resulting filtrate was placed in a clean, dry, and nitrogen gas purged 50 L glass reaction tank. The methylene chloride was removed by distillation until the internal temperature reached 50–53° C. to afford the free-based amine as a thin oil. The tank was then cooled to room temperature and charged with toluene (20 L), chloro-4-(trifluoromethyl) benzene (4200 g, 23.26 mol), and cesium carbonate (7500 g, 23.02 mol). The solution was sparged with nitrogen gas for 1 hour. Near the time of completion of the sparging, fresh catalyst solution was prepared by charging a 2L round-bottom flask, equipped with stir bar and flushed with nitrogen gas, with 2-dicyclohexylphosphino-2'-(N,N-dimethylamino)biphenyl (68 g, 0.17 mol), phenylboronic acid (28 g, 0.23 g), and tetrahydrofuran (1.2 L) followed by palladium acetate (26 g, 0.12 mol). The catalyst solution was stirred at room temperature under nitrogen atmosphere for 15 minutes. The catalyst solution was added to the 50L reaction tank with the use of a cannula (excluding air). The mixture was heated to 79° C. internal temperature under nitrogen atmosphere for 16 hours. The reaction solution was cooled to room temperature and filtered through Celite®. The solids were rinsed with toluene (3×2L) and the filtrate was collected. All filtrates were combined to afford a crude solution of the title compound.

EXAMPLE 2

(3R)-3-(4-Trifluoromethyl-phenylamino)-pentanoic Acid Amide

Aqueous sulfuric acid (8.2 L sulfuric acid and 1.1 L water premixed and cooled to 35 ° C. or less) was added to the crude toluene solution of (3R)-3-(4-trifluoromethyl-phenylamino)-pentanenitrile from Example 1. The resulting bilayer was stirred well and heated to 35° C. for 17 hours. The lower aqueous layer was collected and quenched with aqueous sodium hydroxide (95 L water and 10.7 kg sodium hydroxide) and diisopropyl ether (IPE) (40 L). After extraction and removal of the aqueous layer, the organic layer was combined and extracted with saturated aqueous $NaHCO_3$ (10 L). The organic phase from the resulting bilayer was concentrated by distillation to a volume of 19 L. The solution was then cooled to room temperature and seeded with (3R)-3-(4-trifluoromethyl-phenylamino)-pentanoic acid amide and allowed to granulate for 3 hours while stirring. To the heterogenous mixture was added cyclohexane (38 L) and the mixture was granulated for an additional 11 hours. The solids were filtered, rinsed with cyclohexane (4 L), dried under vacuum at 40° C. to afford 3021 g (75%) of the title compound.

$^1$H NMR (400 MHz, $CDCl_3$): 0.98 (t, 3, J=7.5), 1.60–1.76 (m, 2), 2.45 (d, 2, J=5.8), 3.73–3.80 (m, 1), 5.53(br s, 1), 5.63 (br s, 1), 6.65, (d, 2, J=8.7), 7.39 (d, 2, J=8.7)

$^{13}$C NMR (100 MHz, $CDCl_3$): 10.74, 27.80, 40.02, 51.95, 112.63, 118.9 (q, J=32.7), 125.18 (q, J=271.0), 126.93 (q, J=3.8), 150.17, 174.26

EXAMPLE 3

(3R)-[3-(4-Trifluoromethyl-phenylamino)-pentanoyl]-carbamic Acid Methyl Ester

A clean, dry and nitrogen gas purged 100 L glass tank was charged with (3R)-3-(4-trifluoromethyl-phenylamino)- pentanoic acid amide (6094 g, 23.42 mol), isopropyl ether (30 L) and methyl chloroformate (2.7 kg, 29 mol). The resulting slurry was cooled to 2° C. The reaction tank was then charged with lithium t-butoxide solution (18–20% in THF, 24.6 kg, ~58 mol) at such a rate as to maintain the internal temperature below 10° C. and preferably at a temperature of about 5° C. Ten minutes after addition of base was complete, the reaction was quenched by the addition of 1.5 M hydrochloric acid (36 L). The aqueous layer was removed, and the organic phase extracted with saturated NaCl/water solution (10 L). The aqueous layer was removed and the organic phase was concentrated by distillation under vacuum and at a temperature of about 50° C. until the volume was reduced to about 24 L. Cyclohexane (48 L) was added to the reaction vessel and distillation was again repeated at an internal temperature of about 45–50° C. under vacuum until the volume of solution in the vessel was reduced to 24 L. A second portion of cyclohexane (48 L) was added to the reaction vessel and distillation was again repeated at an internal temperature of about 45–50° C. under vacuum until the volume of solution in the vessel was reduced to 24 L. While holding the temperature at 50° C., the solution was seeded with (3R)-[3-(4-trifluoromethyl-phenylamino)-pentanoyl]-carbamic acid methyl ester and allowed to granulate while stirring for 2 hours. The solution was then cooled slowly (over 1.5 hours) to room temperature and allowed to granulate while stirring for 15 hours. The mixture was filtered. The resulting solids were rinsed with cyclohexane (10 L) and dried under vacuum at 40° C. to afford 7504 g of the title compound (94%).

m.p.=142.3–142.4° C.

$^1$H NMR (400 MHz, $d_6$-Acetone): 0.96 (t, 3, J=7.4), 1.55–1.75 (m, 2), 2.86 (dd, 1, J=6.6, 16.2, 2.96 (dd, 1, J=6.2, 16.2), 3.69 (s, 3), 3.92–3.99 (m, 1), 5.49 (br d, 1, J=8.7), 6.76 (d, 2, J=8.7), 7.37 (d, 2, J=8.7), 9.42 (br s, 1).

$^{13}$C NMR (100 MHz, $CDCl_3$): 10.62, 28.10, 40.19, 51.45, 53.42, 112.54, 118.98 (q, J=32.70), 125.16 (q, J=270.2), 126.90 (q, J=3.8), 150.10, 152.71, 173.40.

EXAMPLE 4

(2R, 4S)-(2-Ethyl-6-trifluoromethyl-1,2,3,4-tetrahydro-quinolin-4-yl)-carbamic Acid Methyl Ester A clean, dry and nitrogen gas purged 100 L glass tank was charged (3R)-[3-(4-trifluoromethyl-phenylamino)-pentanoyl]-carbamic acid methyl ester (7474 g) followed by 2B ethanol (46 L) and water (2.35 L). Sodium borohydride (620 g) was added to the solution in one portion. Nitrogen gas purging is maintained. The mixture was stirred at room temperature for 20 minutes and then cooled to −10° C. A solution of 3.3 M aqueous magnesium chloride solution (4.68 kg $MgCl_2.6H_2O$ in 7 L water) was added at such a rate that the internal temperature did not exceed −5° C. Once addition was completed, the reaction solution was warmed to 0° C. for 45 min. The reaction was quenched by transferring the reaction mixture to a 200 L tank containing methylene chloride (70 L), and 1M hydrochloric acid/citric acid solution (5.8 L concetrated hydrochloric acid, 64 L water, and 10.5 kg citric acid). The headspace of the tank was purged with nitrogen gas. This bilayer was stirred at room temperature for two hours. The phases were separated and the lower organic product layer was removed. After aqueous layer removal, the organic phase was returned to the reaction vessel and extracted with an aqueous citric acid solution (6.3 kg citric acid, 34 L water). The mixture was stirred for 1 hour and allowed to settle overnight. The layers were separated and to the organic was added Darco® activated carbon (G-60 grade, 700 g) (Atlas Powder Co., Wilmington, Del.) and the solution was stirred for 30 minutes. The mixture was then filtered through Celite®, and the carbon was rinsed twice with methylene chloride (14L and 8L). The filtrate was distilled while periodically adding hexanes so as to displace the methylene chloride with hexanes to a total final volume of 70 L (112 L total hexanes used). Product crystallized during the displacement. Once a stable distillation temperature was reached, the solution was cooled and granulated while stirring at room temperature for 10 hours. The solids were filtered off, rinsed with hexanes (14 L), and dried at 40° C. under vacuum to afford the title compound (5291 g). (80%).

m.p.=139.0–140.5° C.

$^1$H NMR (400 MHz, $d_6$-Acetone): 1.00 (t, 3, J=7.5), 1.51–1.67 (m, 3), 2.19 (ddd, 1, J=2.9, 5.4, 12.4), 3.44–3.53 (m, 1), 3.67 (s, 3), 4.89–4.96(m, 1), 5.66 (br s, 1), 6.56 (br d, 1, J=8.7), 6.65 (d, 1, J=8.7), 7.20 (d, 1, J=8.7), 7.30 (br s, 1).

$^{13}$C NMR (100 MHz, $CDCl_3$): 9.88, 29.24, 35.47, 48.09, 52.42, 52.60, 113.66, 118.90 (q, J=33.1), 121.40, 124.08 (q, J=3.8), 125.08 (q, J=270.6), 125.70 (q, J=3.8), 147.68, 157.30.

EXAMPLE 5

(2R. 4S)-2-Ethyl-4-methoxycarbonylamino-6-trifluoromethyl-3,4-dihydro-2H-quinoline-1-carboxylic Acid Ethyl Ester A clean, dry and nitrogen gas purged 100 L glass tank was charged with (2R, 4S)-(2-ethyl-6-trifluoromethyl-1,2,3,4-tetrahydro-quinolin-4-yl)-carbamic acid methyl ester (5191 g, 17.17 mol), methylene chloride (21 L), and pyridine (4.16 L, 51.4 mol). The reaction vessel was cooled to −10° C. Ethyl chloroformate (4.10 L, 42.9 mol) was slowly added at such a rate that the internal temperature did not exceed −5° C. The reaction solution was brought to 0° C. and held for 20 hours. The reaction was quenched by adding to a mixture of diisopropyl ether (IPE) (36 L), methylene chloride (6.2 L) and 1.5M hydrochloric acid solution (52 L). The resulting phases were separated and the organic layer was extracted with 1M sodium hydroxide solution (15 L). The resulting phases were separated and the organic layer was washed with saturated aqueous sodium chloride NaCl (15 L). The resulting phases were separated and the organic layer was concentrated by distillation to a volume of 40 L. Crystallization initiated at lower volume. The methylene chloride was displaced with IPE by distilling the mixture and periodically adding IPE to maintain a constant volume at 40L until a temperature of 68° C. was maintained (46 L total IPE used). The mixture was cooled and allowed to granulate with stirring at room temperature for 19 hours. The solids were filtered, rinsed with IPE (8 L), and dried under vacuum at 40° C. to afford 5668 g of the title compound (88%).

m.p.=157.3–157.6° C.

$^1$H (400 MHz, $d_6$-Acetone): 0.84 (t, 3, J=7.5), 1.26 (t, 3, J=7.0), 1.44–1.73 (m, 3), 2.59 (ddd, 1, J=4.6, 8.3, 12.9), 3.67 (s, 3), 4.14–4.28 (m, 2), 4.46–4.54 (m, 1), 4.66–4.74 (m, 1), 6.82 (br d, 1, J=9.1), 7.53 (s, 1), 7.58 (d, 1, J=8.3), 7.69 (d, 1, J=8.3).

$^{13}$C NMR (100 MHz, $CDCl_3$): 9.93, 14.55, 28.46, 38.08, 46.92, 52.64, 53.70, 62.42, 120.83 (q, J=3.4), 124.32 (q, J=271.7), 124.36 (q, J=3.4), 126.38, 126.46 (q, J=32.7), 134.68, 139.65, 154.66, 156.85.

EXAMPLE 6

(2R, 4S)-4-[(3,5-Bis-trifluoromethyl-benzyl)-methoxycarbonyl-amino]-2-ethyl-6-trifluoromethyl-3,4-dihydro-2H-quinoline-1-carboxylic Acid Ethyl Ester A clean, dry and nitrogen gas purged 100 L glass tank was charged with (2R, 4S)-2-ethyl-4-methoxycarbonylamino-6-trifluoromethyl-3,4-dihydro-2H-quinoline-1-carboxylic acid ethyl ester (5175 g, 13.82 mol), $CH_2Cl_2$ (20 L), and potassium t-butoxide (1551 g, 13.82 mol) at room temperature. The mixture was stirred for five minutes. 3,5-Bis(trifluromethyl)benzylbromide (3.50 L, 19.1 mol) was added to the mixture in one portion. The internal temperature was maintained between 20–25° C. for 1.5 hours. After 2.3 hours of reaction time, an additional charge of potassium t-butoxide (46.10 g, 0.41 mol) was added. After a total reaction time of 4.5 hours, the reaction was quenched. 1,4-Diazabicyclo[2.2.2]octane (DABCO) (918 g, 8.18 mol) was added to the reaction solution and the mixture was stirred for 1 hour. IPE (40 L) and 0.5 M hydrochloric acid (30 L) were added to the reaction mixture. The resulting organic and aqueous phases were separated and the organic layer was extracted with 0.5M hydrochloric acid (2×30 L). The resulting organic and aqueous phases were then separated and the organic layer was extracted with saturated aqueous sodium chloride (15 L) and the resulting organic and aqueous phases were separated. Anhydrous magnesium sulfate (3.5 kg) was added to the organic layer and the mixture was stirred for 30 minutes. The mixture was then filtered (0.5 micron filter) into a 50 L glass tank with IPE wash (8 L) in two portions. The filtrate was concentrated under vacuum to a total volume of 12 L with internal temperature of 35° C. resulting in an oil. 2B Ethanol (25 L) was added to the oil and the solution was concentrated under vacuum to a volume of 12 L. To the solution was added 2B ethanol (15 L) and the solution was again concentrated under vacuum to a volume of 12 L. The solution was cooled to room temperature and seeded with (2R, 4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (3 g). The solution was granulated for about 38 hours, filtered, and rinsed with 2B ethanol (4 L+2L). The solids were dried under vacuum (no heat) to afford 4610 g (55%) of the title compound. The mother liquor from the above filtration was concentrated under vacuum (solution temp=62° C.) to a final volume of 6 L and cooled to 38° C. The solution was seeded with (2R, 4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (0.5 g) and allowed to cool and granulate while stirring for 19 hours. The mixture was filtered and the solids rinsed with 2B EtOH (2.5 L). The resulting cake was dried under vacuum (no heat) to provide 1422 g (17%) of the title compound as the second crop. Combined recovery was 6032 g (73%).

EXAMPLE 7

(3R)-[3-(4-Trifluoromethyl-phenylamino)-pentanoyl]-carbamic Acid Benzyl Ester A clean, dry and nitrogen gas purged flask was charged with (3R)-3-(4-trifluoromethyl-phenylamino)-pentanoic acid amide (20.11 g, 77.27 mmol) and isopropyl ether (100 mL) and the mixture was cooled to −12° C. Benzyl chloroformate (13.25 mL, 92.8 mmol) was then added followed by the slow addition of 1.0 M lithium tert-butoxide in THF solution (185.5 mL). The lithium tert-butoxide solution was added at such a rate that the internal temperature remained below 0° C. Fifteen minutes after the completion of base addition, the reaction was quenched by adding the mixture to isopropyl ether (100 mL) and 1.5 M hydrochloric acid (130 mL). The phases were separated and the organic layer was washed with saturated aqueous sodium chloride solution (130 mL). The phases were separated, the organic layer was dried ($MgSO_4$), filtered, and concentrated under partial vacuum (at 40° C.) to a total volume of 100 mL. Additional isopropylether (200 mL) was added and the solution was again concentrated under partial vacuum (at 40° C.) to a total volume of 100 mL. After cooling, the solution was seeded with (3R)-[3-(4-trifluoromethyl-phenylamino)-pentanoyl]-carbamic acid benzyl ester and allowed to stir at room temperature overnight. The remaining solvent was displaced with cyclohexane using partial vacuum distillation (45° C. bath, 200 mL followed by 100 mL), the resultant slurry was cooled and stirred for 40 minutes, filtered, and dried to provide 25.8714 g (85%) of the title compound.

m.p. 100.6–101.4° C.

$^1H$ NMR (400 MHz $d_6$-acetone): 0.96 (t, 3, J=7.5), 1.57–1.75 (m, 2), 2.87 (dd, 1, J=6.6, 16.2), 2.97 (dd, 1, J=6.2, 16.2), 3.94–4.00 (m, 1), 5.16 (s, 2), 5.50 (br s, 1), 6.75 (d, 2, J=5.7), 7.33–7.43 (m, 7), 9.52 (br s, 1).

$^{13}C$ NMR (100 MHz $CDCl_3$): 10.66, 28.13, 40.28, 51.47, 68.25, 112.52, 118.91 (q, J=32.3), 125.21 (q, J=269.9), 126.92 (q, J=3.8), 128.64, 128.98, 129.04, 135.05, 150.12, 152.12, 173.52.

EXAMPLE 8

(2R, 4S)-(2-Ethyl-6-trifluoromethyl-1,2,3,4-tetrahydro-quinolin-4-yl)-carbamic Acid Benzyl Ester A clean, dry and nitrogen gas purged flask was charged with (3R)-[3-(4-trifluoromethyl-phenylamino)-pentanoyl]-carbamic acid benzyl ester (11.51 g, 29.18 mmol) and 95% ethanol (80 mL) and the solution was cooled in an ice/acetone bath (∼−12° C.). Sodium borohydride (0.773 g, 20.4 mmol) was then added to the solution. The internal temperature of the reaction was −11.5° C. To the reaction flask was slowly added a solution of $MgCl_2.6H_2O$ (6.23 g, 30.6 mmol, in 13 mL $H_2O$). The internal temperature was maintained below −5° C. by adjusting the addition rate. Once all of the magnesium solution was added, the solution temperature was raised to 0° C. and stirred for 30 minutes. The reaction was then quenched by the addition of methylene chloride (115 mL), 1N hydrochloric acid (115 mL) and citric acid (14.02 g, 72.97 mmol). This bilayer was stirred at room temperature. After 3.75 hours, the cyclization reaction was found to be complete by HPLC analysis and the phases were separated. Water (58 mL) and citric acid (8.41 g, 43.77 mmol) were added to the organic layer and the mixture was stirred at room temperature for 45 minutes. The phases were separated and g-60 Darco® activated charcoal (1.52 g) (Atlas Powder Co., Wilmington, Del.) was added to the organic layer. After stirring for 45 minutes, the solution was filtered through Celite® and washed with methylene chloride (2×15 mL). The filtrate was then displaced with hexanes (approximately 350 mL) by distillation under atmospheric pressure and concentration of the mixture to a total volume of 230 mL. The mixture was stirred at room temperature for 14 h, filtered, and dried to afford 9.0872 g (82%) of the title compound.

m.p. 154.0–155.2° C.

$^1$H NMR (400 MHz d$_6$-acetone): 1.00 (t, 3, J=7.5), 1.51–1.69 (m, 3), 2.17–2.26 (m, 1), 3.46–3.54 (m, 1), 4.96 (ddd, 1, J=5.4, 9.5, 11.6), 5.14 (d, 1, J=12.9), 5.20 (d, 1, J=12.9), 5.66 (br s, 1), 6.65 (d, 1, J=8.3), 6.71 (br d, 1, J=9.1), 7.20 (dd, 1, J=1.9, 8.9), 7.30–7.43 (m, 6).

$^{13}$C NMR (100 MHz CDCl$_3$): 9.89, 29.24, 35.34, 48.16, 52.44, 67.27, 113.70, 118.85 (q, J=32.7), 121.37, 124.12 (q, J=3.8), 125.14 (q, J=270.6), 125.72 (q, J=3.8), 128.38, 128.51, 128.86, 136.57, 147.71, 156.74.

EXAMPLE 9

(R)-3-Aminopentanenitrile Methanesulfonic Acid Salt

Step 1: Methanesulfonic Acid 2-tert-butoxycarbonylamino-butyl Ester.

Run #1: BOC anhydride (515.9 g) in ethyl acetate (400 mL) was added to a solution of R-(-)-2-amino-1-butanol (200.66 g) in ethyl acetate (1105 mL) via an addition funnel. The reaction mixture was stirred for approximately 30 minutes. Tetramethylethylenediamine (TMEDA) (360 mL) was added and the reaction mixture was cooled to approximately 10° C. Methanesulfonyl chloride (184.7 mL) was added to the reaction mixture over a 30-minute period. After stirring for 1 hour, the reaction mixture was filtered and the filtrate was collected.

Run #2: BOC anhydride (514.5 g) in ethyl acetate (400 mL) was added to a solution of R-(-)-2-amino-1-butanol (200.12 g) in ethyl acetate (1101 mL) via an addition funnel. The reaction mixture was stirred for approximately 30 minutes. Tetramethylethylenediamine (TMEDA) (359.1 mL) was added and the reaction mixture was cooled to approximately 10° C. Methanesulfonyl chloride (184.1 mL) was added to the reaction mixture over a 30-minute period. After stirring for 1 hour, the reaction mixture was combined with the filtrate from Run # 1 and filtered. The solids where washed with 400 mL ethyl acetate. Hexanes (12 L) were added to the filtrate. The mixture was cooled in an ice/water bath. After about 2.5 hours the solids were isolated by filtration, washed with hexanes (2 L) and dried under vacuum to afford the title compound (971.57 g).

Step 2: (1-Cyanomethyl-propyl)-carbamic Acid tert-butyl Ester.

Sodium cyanide (24.05 g) was added to dimethylformamide (DMF) (500 L) and the mixture was stirred at 35° C. for 30 minutes. Tetrabutyl ammonium bromide was added and the reaction mixture was stirred at 35° C. for two hours. Methanesulfonic acid 2-tert-butoxycarbonylamino-butyl ester (101.23 g) was added and the reaction mixture was stirred at 35° C. overnight. The mixture was then partitioned between two liters water and one liter isopropyl ether. The resulting organic and aqueous phases were separated and washed sequentially with watner and a saturated solution of sodium chloride in water. The organic layer was dried over magnesium sulfate, filtered and concentrated to afford a solid (65.22 g). The solid (61.6 g) was transferred to a flask equipped with an overhead stirrer. Hexane was added and the flask was heated to 65° C. After all the solids were in solution, the mixture was cooled to ambient temperature. The mixture was stirred overnight. The resulting solids were isolated by filtration to afford the title compound (52.32 g).

Step 3: (R)-3-Aminopentanenitrile Methanesulfonic Acid Salt.

Methane sulfonic acid (71 g) was added to a solution of (1-cyanomethyl-propyl)-carbamic acid tert-butyl ester in tetrahydrofuran (530 mL). The reaction mixture was heated to 40° C. for approximately 30 minutes. The temperature was raised to 45° C. and stirred for approximately one hour. The temperature was raised again to 65° C. and the reaction mixture was stirred for five hours. The mixture was allowed to cool to ambient temperature. The resulting solids were isolated by filtration to afford the title compound (41.53 g).

What is claimed is:

1. The compound of formula III,

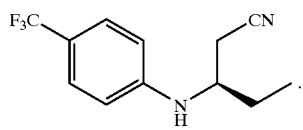

2. The compound of formula IV,

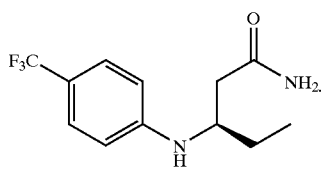

3. A compound of formula VI,

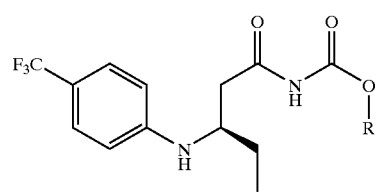

wherein R is selected from methyl, benzyl and substituted benzyl.

4. A compound of formula VII,

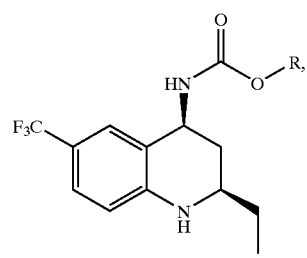

wherein R is selected from methyl, benzyl and substituted benzyl.

5. A compound of claim 3 or 4 wherein R is selected from methyl, benzyl and benzyl substituted with one or more substituents each independently selected from (C$_1$–C$_3$)alkyl, (C$_1$–C$_3$)alkyloxy and a halogen.

6. A method for preparing the compound of formula III,

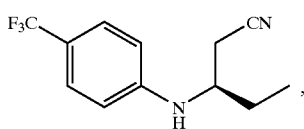

comprising coupling trifluoromethylbenzene that is para-substituted with a halogen or O-triflate with the compound of formula II,

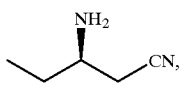

to form the compound of formula III.

7. A method of claim 6 wherein said coupling comprises combining said trifluoromethylbenzene compound with said compound of formula II in the presence of a transition metal.

8. A method of claim 7 wherein said transition metal is palladium.

9. A method of claim 6 wherein said trifluoromethylbenzene compound is combined with said compound of formula II in the presence of a phosphine ligand.

10. A method of claim 9 wherein said phosphine ligand is a dialkylphosphinobiphenyl ligand.

11. A method of claim 10 wherein said phosphine ligand is selected from 2-dicyclohexylphosphino-2'-(N,N-dimethylamino)biphenyl and 2-dicyclohexylphosphino-2'-methylbiphenyl.

12. A method of claim 6 wherein said coupling comprises combining said trifluoromethylbenzene compound with said compound of formula II in the presence of a base.

13. A method of claim 12 wherein said base is cesium carbonate.

14. A method for preparing the compound of formula IV,

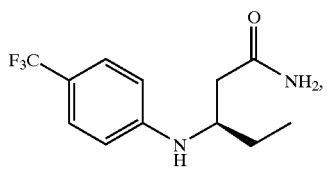

comprising hydrolyzing the compound of formula III,

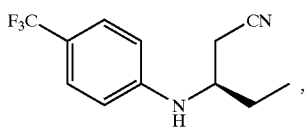

with a hydrolyzing agent selected from an acid and a base to form the compound of formula IV.

15. A method of claim 14 wherein said hydrolyzing agent is an acid.

16. A method of claim 15 wherein said acid comprises sulfuric acid with water.

17. A method for preparing a compound of formula VI,

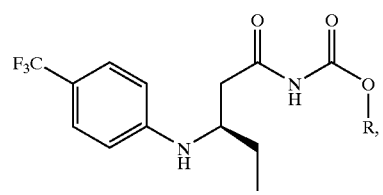

comprising combining the compound of formula IV,

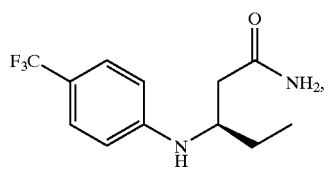

with a compound of formula V,

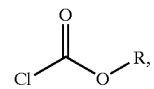

wherein R is selected from methyl, benzyl and substituted benzyl, in the presence of a base to form a compound of formula VI.

18. A method of claim 17 wherein said base is lithium t-butoxide.

19. A method for preparing a compound of formula VII,

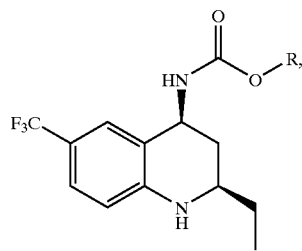

comprising reducing a compound of formula VI,

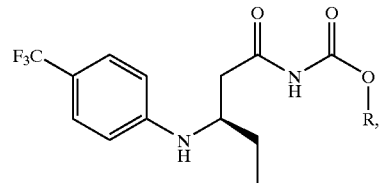

wherein R is selected from methyl, benzyl and substituted benzyl, with a reducing agent to form a reduced compound and cyclizing the reduced compound under acidic conditions to form a compound of formula VII.

20. A method of claim 19 wherein said reducing agent is sodium borohydride in the presence of a Lewis acid.

21. A method of claim 20 wherein said Lewis acid is selected from calcium ions and magnesium ions.

* * * * *